United States Patent
Imamura (10) Patent No.: US 10,440,805 B2
(45) Date of Patent: Oct. 8, 2019

(54) RADIATION IRRADIATION DEVICE

(71) Applicant: FUJIFILM Corporation, Tokyo (JP)

(72) Inventor: Ryo Imamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/628,567

(22) Filed: Jun. 20, 2017

(65) Prior Publication Data

US 2018/0014396 A1  Jan. 11, 2018

(30) Foreign Application Priority Data

Jul. 6, 2016  (JP) ................................. 2016-134146

(51) Int. Cl.
| | |
|---|---|
| H05G 1/26 | (2006.01) |
| H05G 1/32 | (2006.01) |
| A61B 6/00 | (2006.01) |
| H05G 1/58 | (2006.01) |

(52) U.S. Cl.
CPC ........... *H05G 1/265* (2013.01); *A61B 6/4405* (2013.01); *A61B 6/56* (2013.01); *H05G 1/32* (2013.01); *H05G 1/58* (2013.01); *A61B 2560/0214* (2013.01)

(58) Field of Classification Search
None
See application file for complete search history.

(56) References Cited

U.S. PATENT DOCUMENTS

| | | | | |
|---|---|---|---|---|
| 5,530,362 | A * | 6/1996 | Boehm | G01R 31/3606 324/427 |
| 5,594,345 | A * | 1/1997 | Boehm | A61B 6/4405 320/132 |
| 5,680,027 | A * | 10/1997 | Hiratsuka | G01R 31/3624 307/150 |
| 6,298,116 | B1 | 10/2001 | Methley et al. | |
| 2008/0170666 | A1 * | 7/2008 | Coombs | A61B 6/4405 378/101 |
| 2008/0258895 | A1 * | 10/2008 | Yamaguchi | G07C 5/0816 340/455 |

(Continued)

FOREIGN PATENT DOCUMENTS

| | | |
|---|---|---|
| JP | S61126800 | 6/1986 |
| JP | 2000270493 | 9/2000 |

(Continued)

OTHER PUBLICATIONS

"Office Action of Japan Counterpart Application," dated on Aug. 6, 2019, with English translation thereof, p. 1-7.

*Primary Examiner* — Michael J Logie
(74) *Attorney, Agent, or Firm* — JCIPRNET (57) ABSTRACT

The invention provides a radiation irradiation device that can appropriately manage the residual capacity of a battery without being influenced by the internal resistance of the battery. The radiation irradiation device includes a radiation generating part that generates radiation; a battery part that supplies electric power to the radiation generating part; and a residual capacity calculation part that calculates the residual capacity of the battery part. The residual capacity calculation part calculates the residual capacity of the battery part on the basis of a current flowing into the battery part, an internal resistance of the battery part, and a voltage of the battery part.

15 Claims, 7 Drawing Sheets

(56) References Cited

U.S. PATENT DOCUMENTS

| | | | |
|---|---|---|---|
| 2010/0019720 A1* | 1/2010 | Liu | A61B 6/4233 320/107 |
| 2011/0110498 A1 | 5/2011 | Takae et al. | |
| 2011/0293070 A1* | 12/2011 | Kamiya | A61B 6/4283 378/102 |
| 2011/0301891 A1* | 12/2011 | Kim | B60L 3/0046 702/63 |
| 2011/0317817 A1* | 12/2011 | Nishino | A61B 6/4405 378/102 |
| 2012/0121952 A1* | 5/2012 | Majima | G01R 31/3679 429/90 |
| 2013/0223596 A1* | 8/2013 | Kojima | A61B 6/4405 378/102 |
| 2016/0043580 A1* | 2/2016 | Rush, Jr. | H02J 7/0021 320/101 |
| 2017/0000429 A1* | 1/2017 | Nose | A61B 6/105 |
| 2017/0020480 A1* | 1/2017 | Hishikawa | A61B 6/4405 |

FOREIGN PATENT DOCUMENTS

| | | | | |
|---|---|---|---|---|
| JP | 2003504798 | | 2/2003 | |
| JP | 2004022308 | | 1/2004 | |
| JP | 2007053005 A | * | 3/2007 | ............ H01M 10/48 |
| JP | 2008265518 | | 11/2008 | |
| JP | 2008292380 | | 12/2008 | |
| JP | 2014150948 | | 8/2014 | |
| WO | 9410718 | | 5/1994 | |
| WO | 2010004855 | | 1/2010 | |

\* cited by examiner

RADIATION IRRADIATION DEVICE

CROSS-REFERENCE TO RELATED APPLICATIONS

The present application claims priority under 35 U.S.C. § 119 to Japanese Patent Application No. 2016-134146, filed on Jul. 6, 2016. Each of the above application(s) is hereby expressly incorporated by reference, in its entirety, into the present application.

BACKGROUND OF THE INVENTION

1. Field of the Invention

The present invention relates to a radiation irradiation device having a radiation source that receives electric power supply from a battery.

2. Description of the Related Art

In the related art, portable radiation irradiation devices used in a case where a patient's radiation image are captured in operating rooms, examination rooms, or inpatient rooms have been suggested variously.

The portable radiation irradiation devices basically include a leg part enabled to travel by wheels, a main body part that houses a control part consisting of a battery for driving a radiation source, an electric circuit related to the driving of the radiation source, and the like and is held on the leg part, and an arm part connected to the main body part, and are configured by attaching the radiation source to a tip of the arm part.

When such radiation irradiation devices are used, a radiation irradiation device is first moved to the vicinity of a patient's bed. Next, the radiation source is moved to a desired position, and a radiation detector is moved to a desired position behind a subject. Then, in this state, the subject is irradiated with radiation by driving the radiation source, and a radiation image of the subject is acquired by detecting the radiation transmitted through the subject using the radiation detector.

Here, in the related art, in the portable radiation irradiation devices, a battery using a storage battery is used as a power source (refer to JP2014-150948A, JP2003-504798A, and JP1986-126800A (JP-S61-126800A). As a method of managing the residual capacity of such a battery, there is a method of monitoring the terminal voltage of the battery.

SUMMARY OF THE INVENTION

However, for example, in a case where a lithium ion battery is used, the internal resistance of the battery is large. Therefore, in a case where an output current from the battery has changed, a change in the terminal voltage of the battery is large. Additionally, since the internal resistance of the battery changes with lapse of time, the terminal voltage also changes with lapse of time. Hence, whenever the current consumption of a radiation irradiation device changes, the residual capacity of the battery fluctuates, and suitable management of the residual capacity cannot be performed.

Additionally, in a case where a high current flows due to the emission of the radiation from the radiation source, the voltage drop of the terminal voltage of the battery become large. As a result, there is a problem that it is erroneously determined that the residual capacity of the battery become equal to or less than a threshold value, and the radiation irradiation device itself stops.

In addition, although JP2008-292380A and JP2000-270493A have description about the residual capacity management of a lithium ion battery provided in a hybrid car and the clock, nothing is suggested regarding the residual capacity management of the battery of the radiation irradiation device. Additionally, in JP2008-292380A, nothing is taken into consideration about the internal resistance of the battery.

An object of the invention is to provide a radiation irradiation device that can appropriately manage the residual capacity of a battery without being influenced by the internal resistance of the battery, in view of the above problems.

A radiation irradiation device of the invention includes a radiation generating part that generates radiation; a battery part that supplies electric power to the radiation generating part; and a residual capacity calculation part that calculates the residual capacity of the battery part. The residual capacity calculation part calculates the residual capacity of the battery part on the basis of a current flowing into the battery part, an internal resistance of the battery part, and a voltage of the battery part.

Additionally, in the radiation irradiation device of the above invention, the residual capacity calculation part can calculate the internal resistance of the battery part on the basis of a current flowing into the battery part and a voltage of the battery part at a first time point and a current flowing into the battery part and a voltage of the battery part at a second time point different from the first time point.

Additionally, in the radiation irradiation device of the above invention, the residual capacity calculation part can calculate the internal resistance R of the battery part on the basis of the following Expression.

$$R=(V1-V2)/(I1-I2)$$

Here, I1 is the current flowing into the battery part at the first time point, V1 is the voltage of the battery part at the first time point, I2 is the current flowing into the battery part at the second time point and V2 is the voltage of the battery part at the second time point. Additionally, in the radiation irradiation device of the above invention, the residual capacity calculation part can calculate the residual capacity of the battery part in a period other than a generation period of the radiation.

Additionally, the radiation irradiation device of the above invention can further include a radiation exposure switch that receives an emission instruction of the radiation from the radiation generating part, and the residual capacity calculation part can calculate the residual capacity of the battery part in a period other than a period in which the radiation exposure switch is turned on.

Additionally, the radiation irradiation device of the invention can further include a first exposure switch that receives a preparation operation start instruction of the radiation generating part and a second exposure switch that receives an emission instruction of the radiation from the radiation generating part, and the residual capacity calculation part calculates the residual capacity of the battery part in a period other than a period until the second exposure switch is turned off from lapse of a preset period after the first exposure switch is turned on.

Additionally, in the radiation irradiation device of the above invention, the residual capacity calculation part can calculate the internal resistance of the battery part at preset intervals.

Additionally, in the radiation irradiation device of the above invention, the first time point can be a startup time of the radiation irradiation device, and the second time point can be a stable time after the startup of the radiation irradiation device.

Additionally, in the radiation irradiation device of the above invention, the first time point can be during the generation period of the radiation and the second time point can be a period other than the generation period of the radiation.

Additionally, in the radiation irradiation device of the above invention, the first time point can be a period of a normal electric power supply mode and the second time point can be a period of an electric power supply saving mode.

Additionally, the radiation irradiation device of the above invention can further include a notification part that performs notification that the residual capacity of the battery part calculated by the residual capacity calculation part is equal to or less than a preset threshold value.

Additionally, the radiation irradiation device of the above invention can further include a control part that stops the radiation irradiation device in a case where the residual capacity of the battery part calculated by the residual capacity calculation part is equal to or less than a preset threshold value.

The radiation irradiation device of the invention includes the radiation generating part that generates radiation, the battery part that supplies electric power to the radiation generating part, and the residual capacity calculation part that calculates the residual capacity of the battery part on the basis of the current flowing into the battery part, the internal resistance of the battery part, and the voltage of the battery part. Thus, the residual capacity of the battery can be appropriately managed without being influenced by a change in the internal resistance of the battery.

DESCRIPTION OF THE PREFERRED EMBODIMENTS

Figure 1:
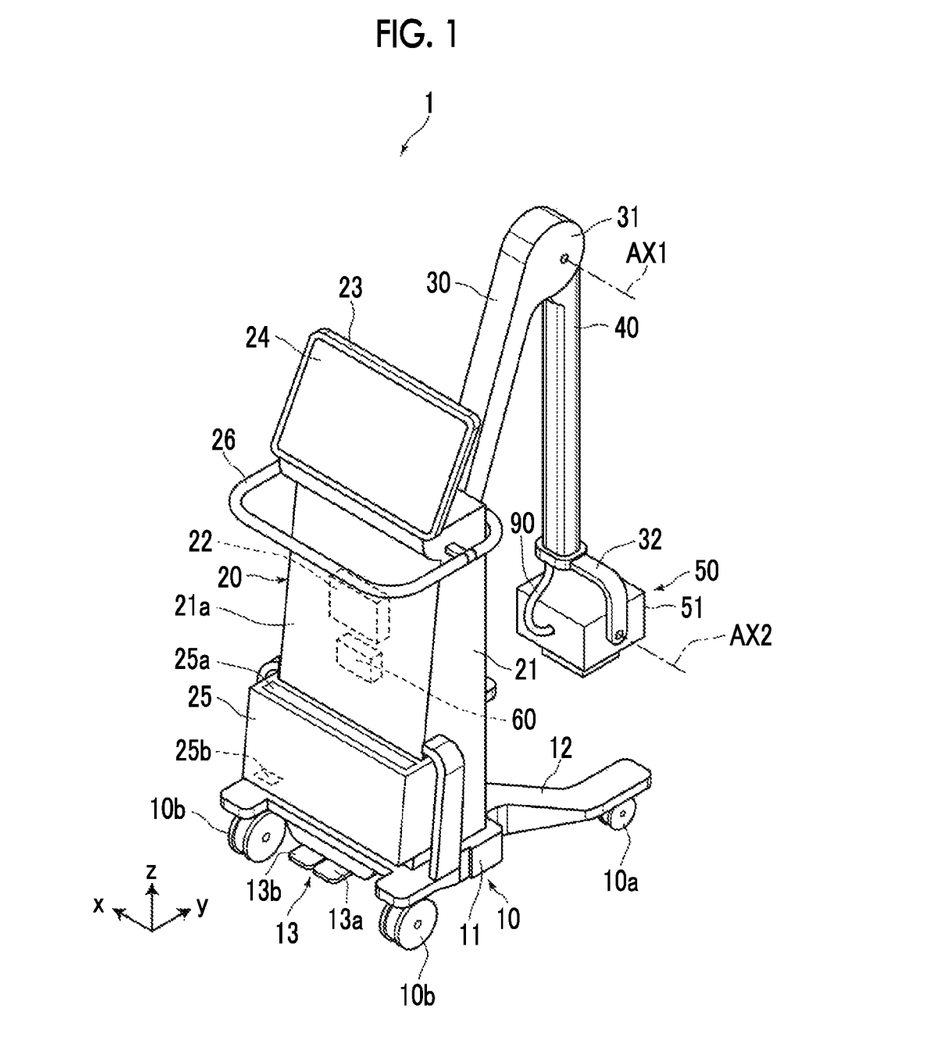
FIG. 1 is a perspective view illustrating an entire shape of a radiation irradiation device of an embodiment of the invention.
Figure 2:
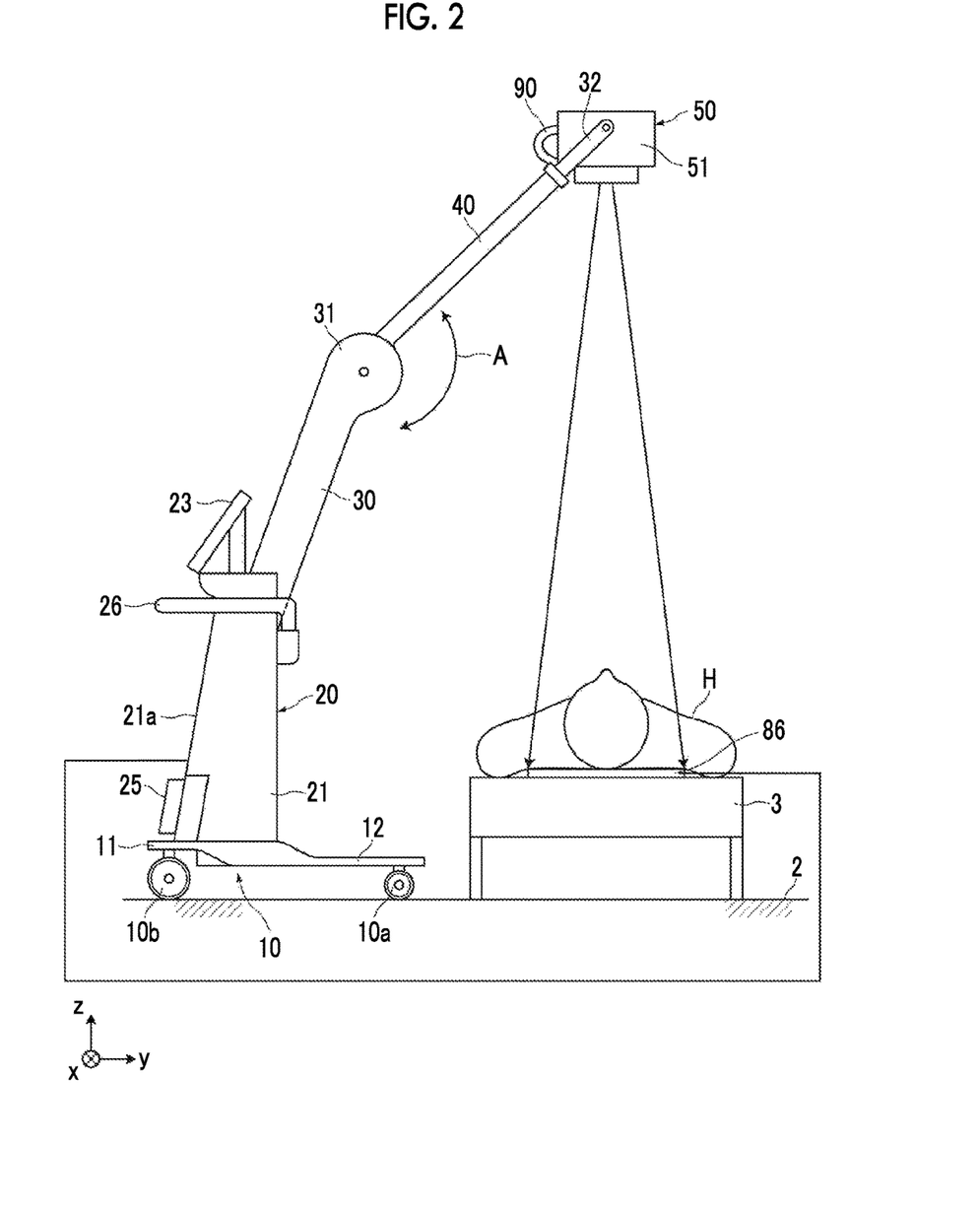
FIG. 2 is a view illustrating the state when the radiation irradiation device of the embodiment of the invention is used.

Hereinafter, a radiation irradiation device of an embodiment of the invention will be described in detail, referring to the drawings. Although the invention has a feature a method of calculating the residual capacity of the battery part provided in the radiation irradiation device, the entire configuration of the radiation irradiation device will first be described. FIG. 1 is a perspective view illustrating the entire shape of the radiation irradiation device of the present embodiment when being not used, and FIG. 2 is a side view illustrating the state when the radiation irradiation device of the present embodiment is used. In addition, in the following, an upper side and a lower side in the vertical direction in a state where the radiation irradiation device is placed on, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a leftward-rightward direction of the radiation irradiation device is defined as an x direction, and a forward-backward direction of the radiation irradiation device is defined as a y direction. In addition, the front herein means a side to which an arm part extends from a main body part of the radiation irradiation device when the device is used.

As illustrated in FIGS. 1 and 2, a radiation irradiation device 1 of the present embodiment includes a leg part 10, a main body part 20, a supporting member 30, an arm part 40, and a radiation generating part 50.

Figure 3:
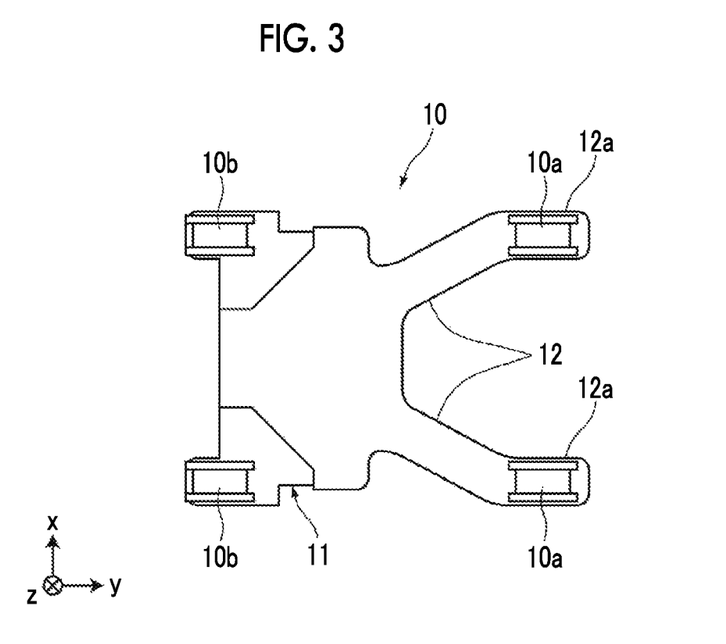
FIG. 3 is a view of a leg part as seen from below.

The leg part 10 is capable of traveling on a device placement surface 2, and consists of a plate-shaped pedestal part 11 on which the main body part 20 is placed, and a foot arm part 12 that extends from the pedestal part 11 toward the front. FIG. 3 is a view of the leg part 10 as seen from below. As illustrated in FIG. 3, the foot arm part 12 is formed in a V shape that widens in the leftward-rightward direction toward the front. First casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle when the leg part 10 is rotated. Thus, handling can be made easy. Additionally, weight reduction can also be achieved.

Each first caster 10a has a shaft that extends in the upward-downward direction, and is attached to the foot arm part 12 such that a rotating shaft of a wheel is revolvable within a horizontal plane about the shaft of the first caster. Additionally, each second caster 10b also has a shaft that extends in the upward-downward direction, and is attached to the pedestal part 11 such that a rotating shaft of a wheel is revolvable within the horizontal plane about the shaft of the second caster. In addition, the rotating shaft of each wheel herein is a rotating shaft when the wheel rotates and travels. The leg part 10 is configured so as to be capable of traveling in an arbitrary direction on the device placement surface 2 by the first casters 10a and the second casters 10b.

Additionally, as illustrated in FIG. 1, a pedal part 13 is provided at the rear of the leg part 10. The pedal part 13 consists of two pedals of a first pedal 13a and a second pedal 13b. The first pedal 13a is a pedal for bringing the second casters 10b into a non-revolvable state. As a user steps on the first pedal 13a, the second casters 10b are configured so as to be locked in revolution by a locking mechanism and brought into the non-revolvable state.

Additionally, the second pedal 13b is a pedal for bringing the second casters 10b into a revolvable state from the non-revolvable state. As the user steps on the second pedal 13b, the second casters 10b are configured so as to be released from the locking by the locking mechanism and brought into the revolvable state again.

A well-known configuration can be used as the locking mechanism that locks the revolution of the second casters 10b. For example, the revolution may be locked such that both sides of the wheels of the second casters 10b are sandwiched by plate-shaped members, or the revolution may be locked by providing members that stop the rotation of shafts of the second caster 10b that extend in the upward-downward direction.

The main body part 20 is placed on the pedestal part 11 of the leg part 10, and includes a housing 21. A control part 22 that controls driving of the radiation irradiation device 1 and a battery part 60 are housed within the housing 21.

The battery part 60 supplies electric power to the radiation generating part 50, a monitor 23, and the radiation detector housed within a cradle 25 to be described below. In addition, the monitor 23 may be configured so as to be attachable to and detachable from the main body part 20. In that case, the battery part 60 supplies electric power to a battery built in the monitor 23 to charge the battery. Additionally, the radiation detector also has a battery built therein, and the battery part 60 supplies electric power to the built-in battery to charge the battery.

Although the battery part 60 includes storage batteries, such as a lead storage battery, a lithium ion battery, a nickel hydride battery, and a NaS battery, it is preferable to use the lithium ion battery from a viewpoint of weight reduction and easy handling. The battery part 60 is connected to an external power source via a connector (not illustrated), and is charged under the supply of electric power from the external power source.

The control part 22 performs control regarding generation and irradiation of radiation, such as a tube current, irradiation time, and a tube voltage, in the radiation generating part 50, and control regarding acquisition of radiation images, such as image processing of a radiation image acquired by the radiation detector to be described below. The control part 22 is configured of, for example, a computer in which a program for control is installed, exclusive hardware, or combination of both.

Figure 4:
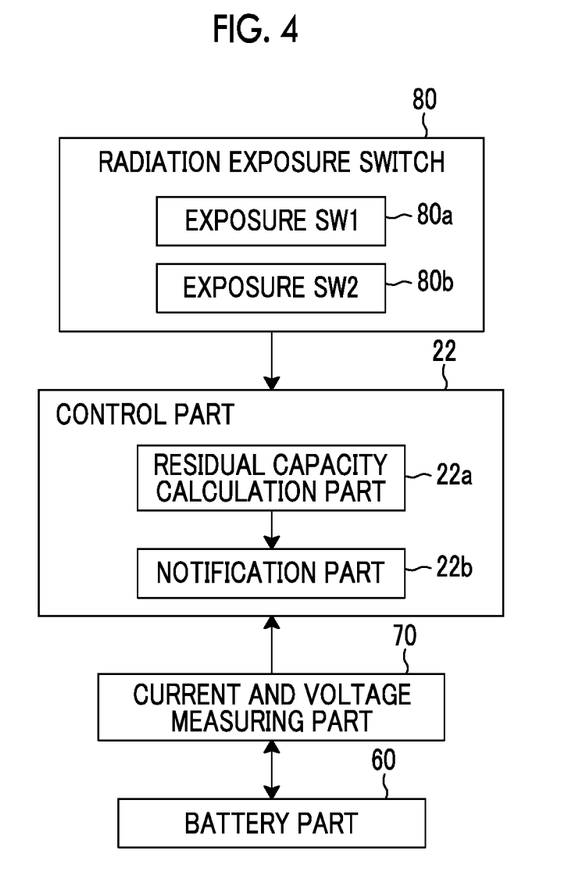
FIG. 4 is a block diagram illustrating the configuration of a control part.

Additionally, the control part 22 calculates the residual capacity of the battery part 60, and in a case where the residual capacity is equal to or less than a preset threshold value, the control part notifies a user of such a situation. Specifically, as illustrated in FIG. 4, the control part 22 includes a residual capacity calculation part 22a and a notification part 22b.

The residual capacity calculation part 22a calculates the residual capacity of the battery part 60 on the basis of a current flowing into the battery part 60, the internal resistance of the battery part 60, and the voltage of the battery part 60. The current and the voltage of the battery part 60 to be used when calculating the residual capacity of the battery part 60 are measured by a current and voltage measuring part 70 illustrated in FIG. 4. The current and voltage measuring part 70 is provided for the battery part 60, and measures the current that flows into the battery part 60 and the terminal voltage of the battery part 60.

Specifically, the residual capacity calculation part 22a calculates a voltage V0 that is not influenced by the internal resistance of the battery part 60 on the basis of the following Expression (1), using a current I and a terminal voltage V of the battery part 60 that are measured by the current and voltage measuring part 70, and an internal resistance R. A relational expression, a table, or the like showing a relationship between the value of the voltage V0 and the residual capacity of the battery part 60 is set in advance in the residual capacity calculation part 22a, and the residual capacity calculation part 22a calculates the residual capacity of the battery part 60, using the relationship.

$$V0 = V + RI \quad (1)$$

In addition, although a preset value may be used for the internal resistance R of the battery part 60, it is known that the internal resistance of the battery part 60 changes over time. Hence, it is desirable to actually measure the internal resistance of the battery part 60 and to update the value of the internal resistance R. In the present embodiment, the internal resistance R of the battery part 60 is periodically calculated at preset intervals. Although it is desirable to set intervals, at which the internal resistance R is calculated to, for example, 2-second intervals, 10-minute intervals may be set.

Specifically, the residual capacity calculation part 22a calculates the internal resistance R of the battery part 60 on the basis of the following Expression (2). In the following Expression (2), I1 is a current flowing into the battery part 60 at a first time point, V1 is a voltage of the battery part 60 at the first time point, I2 is a current flowing into the battery part 60 at the second time point different from the first time point, and V2 is a voltage of the battery part 60 at a second time point. In addition, the currents I1, I2 and the voltages V1, V2 are also measured by the current and voltage measuring part 70.

$$R = (V1 - V2)/(I1 - I2) \quad (2)$$

Additionally, a timing at which the above-described residual capacity of the battery part 60 is calculated and updated and a timing at which the internal resistance R is calculated and updated may be the same timings, or may be different timings. In a case where the different timings are used, the calculated internal resistance R may be stored in a storage medium, such as a semiconductor memory, and may be read from the storage medium at the updating timing of the residual capacity of the battery part 60. In the present embodiment, the timing at which the updating timing of the residual capacity of the battery part 60 and the updating timing of the internal resistance R are set to the same timing. That is, when the residual capacity of the battery part 60 is updated, the current I1, I2 and the voltages V1, V2 of the above Expression (2) are measured, and the internal resistance R is calculated. The updating frequency of the residual capacity of the battery part 60 and the updating frequency of the internal resistance R may be the same frequency or the updating frequency of the internal resistance R may be made smaller.

In addition, in a case where the internal resistance R is calculated on the basis of the above Expression (2), a calculation result is less likely to be affected by an error as a difference between the voltage V1 measured at the first time point and the voltage V2 measured at the second time point is larger, and thus, this case is preferable. Hence, for example, the first time point at which the voltage V1 and the current I1 are measured may be set to a startup time of the radiation irradiation device 1, and the second time point at which the voltage V2 and the current I2 are measured may be set to a stable time after the startup of the device. In addition, the device startup time is a time point while initialization processing of the device is performed, and the stable time of the device is a time point after the initialization processing is completed.

Additionally, the first time point at which the voltage V1 and the current I1 are measured and the second time point at which the voltage V2 and the current I2 are measured are not limited to the above timings. For example, the first time point at which the voltage V1 and the current I1 are measured may be set as during the radiation generation period, and the second time point at which the voltage V2 and the current I2 are measured may be set to as a time point in a period other than the radiation generation period.

Additionally, the first time point at which the voltage V1 and the current I1 are measured may be set to a time point in a period of a normal electric power supply mode, and the second time point at which the voltage V2 and the current I2 are measured may be set to a time point in a period of an electric power supply saving mode. In addition, the normal electric power supply mode is a mode in which electric power is supplied from the battery part 60 to the entire radiation irradiation device 1, and the electric power supply saving mode is a mode in which electric power is kept from being supplied to some components, such as an inverter circuit (not illustrated) that the battery part 60 has, and an irradiation field lamp (not illustrated) showing an irradiation field. Switching between the normal electric power supply mode and the electric power supply saving mode may be automatically performed or may be manually performed.

Additionally, the above-described timings may be combined together regarding the first time point at which the voltage V1 and the current I1 are measured and the second time point at which the voltage V2 and the current I2 are measured. Additionally, an average value may be calculated by calculating the internal resistance R multiple times.

In a case where, as compared to an internal resistance R that is calculated previously, an internal resistance R that is calculated next is an abnormal value, for example, in a case where a difference between the internal resistances R is equal to or more than a preset threshold value, such as a case where the internal resistance R that is calculated next is twice as large as the internal resistance R that is calculated previously, the residual capacity of the battery part 60 may be kept from being updated.

Additionally, as described above, in the present embodiment, the residual capacity of the battery part 60 is periodically updated. However, during the radiation generation period, a high current flows into the battery part 60 and a voltage drop of about 10 V occurs. Therefore, the voltage V of the above Expression (1) changes greatly, the voltage V0 changes, and thus the residual capacity of the battery part 60 cannot be calculated with high accuracy. Meanwhile, since the radiation generation period is as short as several milliseconds to several seconds, it is not necessary particularly to update the residual capacity of the battery part 60 in this period.

Figure 5:
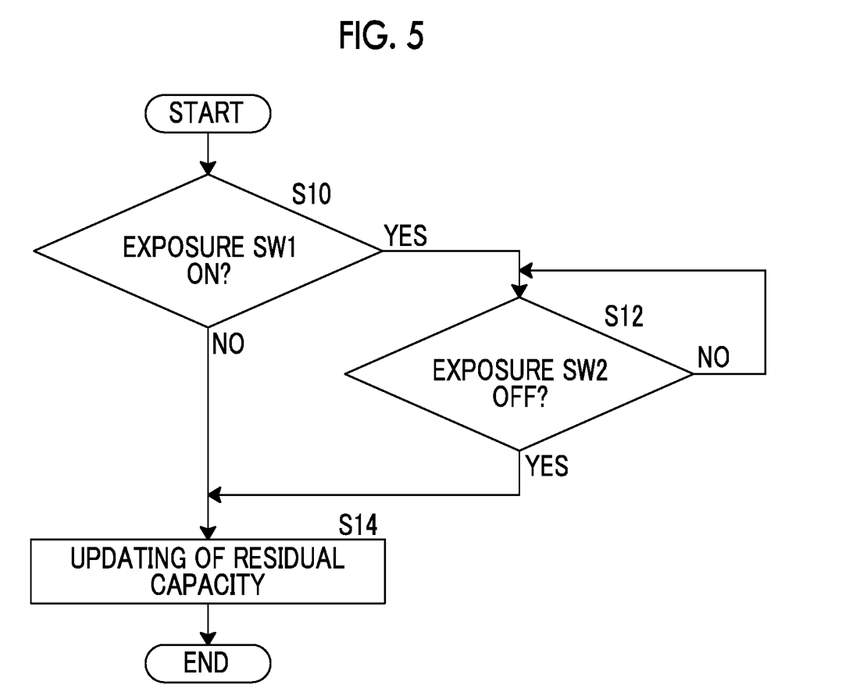
FIG. 5 is a flowchart for explaining an example of a control method in a case where the residual capacity of a battery part is updated in a period other than a radiation generation period.

Hence, the residual capacity of the battery part 60 is not updated in the radiation generation period, but the residual capacity of the battery part 60 may be updated only in a period other than the radiation generation period. FIG. 5 is a flowchart for explaining an example of a control method in a case where the residual capacity of the battery part 60 is updated only in a period other than the radiation generation period.

First, as illustrated in FIG. 4, the radiation irradiation device 1 of the present embodiment includes a radiation exposure switch 80 that receives a user's instruction for generation (exposure) of radiation. The radiation exposure switch 80 includes an exposure SW1 (first exposure switch) that receives a preparation operation start instruction of a radiation generating part 50, and an exposure SW2 (second exposure switch) that receives an emission instruction of the radiation from the radiation generating part 50. In a case where the exposure SW1 is turned on by a user, the preparation operation of the radiation generating part 50 is started, and in a case where the exposure SW2 is further turned on by the user, radiation is emitted from the radiation generating part 50.

When the residual capacity calculation part 22a starts the calculation and the updating of the residual capacity of the battery part 60, as illustrated in FIG. 5, it is checked whether or not the exposure SW1 is in an ON state (S10). Then, in a case where the exposure SW1 is in the ON state (S10, YES), it is further checked whether or not the exposure SW2 is in an OFF state (S12). Then, in a case where the exposure SW2 is in the OFF state (S12, YES), this period is a period other than radiation generation period. Thus, the residual capacity of the battery part 60 is calculated and updated (S14). Meanwhile, in a case where the exposure SW2 is in the ON state (S12, NO), this period is the radiation generation period. Thus, the residual capacity of the battery part 60 is not calculated and updated. In addition, in a case where the exposure SW1 is in the OFF state (S10, NO), this period is a period other than the radiation generation period. Thus, the residual capacity of the battery part 60 is calculated and updated (S14).

Additionally, according to the flowchart illustrated in FIG. 5, the residual capacity of the battery part 60 can be kept from being updated in a period until the exposure SW2 is turned off after the exposure SW1 is turned on. However, the invention is not limited to this. For example, the residual capacity of the battery part 60 may be kept from being updated in a period until the exposure SW2 is turned off from lapse of a preset time (for example, 1300 ms) after the exposure SW1 is turned on. Additionally, for example, the residual capacity of the battery part 60 may be kept from being updated in a period until the exposure SW2 is turned off after being turned on. Additionally, the residual capacity of the battery part 60 may be kept from being updated in a period in which the exposure SW2 is turned off from a time point at which an imaging menu for determining imaging conditions in an input part 24 of the monitor 23 is selected.

In addition, the ending time point of the radiation generation period is not limited to the time point at which the exposure SW2 is turned off and may be a time point at which a preset time (for example, 2 seconds to 3 seconds) has elapsed after a tube voltage of an X-ray tube as the radiation source reaches 0 V.

In addition, in the present embodiment, the two separate switches of the exposure SW1 and the exposure SW2, are provided. However, the configuration of the radiation exposure switch 80 is not limited to this. For example, a switch that receives two push states of half push and full push may be used, a preparation operation of the radiation generating part 50 may be started in the case of the half push, and radiation may be emitted in the case of the full push.

Additionally, the radiation exposure switch 80 may be provided in the input part 24 in the monitor 23 to be described below, or may be provided separately from the monitor 23.

Additionally, in the present embodiment, the residual capacity of the battery part 60 is periodically updated. However, for example, the residual capacity of the battery part 60 may be calculated and updated in a period other than the radiation generation period by updating the residual capacity of the battery part 60 after or before emission of the radiation from the radiation generating part 50. Otherwise, the residual capacity of the battery part 60 may be calculated and updated at the startup time of the radiation irradiation device 1. Additionally, the residual capacity of the battery part 60 may be calculated and updated in a period other than the radiation generation period by combining above-described timings.

Then, the residual capacity of the battery part 60 calculated by the residual capacity calculation part 22a is output to the notification part 22b. Additionally, in a case where the residual capacity is equal to or less than a preset threshold value, the notification part 22b notifies a user of such a situation. Specifically, the notification part 22b of the present embodiment causes the monitor 23 to display that the residual capacity of the battery part 60 is equal to or less than the threshold value. In addition, the configuration of the notification part 22b is not limited to this. For example, light emitting parts, such as light emitting diodes (LEDs), may be provided, and in a case where the residual capacity of the battery part 60 is equal to or less than the threshold value, the notification part 22b causes the light emitting parts to emit light.

Additionally, in a case where the residual capacity of the battery part 60 is equal to or less than the preset threshold value, not only a user may be informed of such a situation as described above, but also the above-described control part 22 may stop the operation of the radiation irradiation device 1.

Returning to FIGS. 1 and 2, the radiation generating part 50 is a so-called mono-tank in which a radiation source, a booster circuit, a voltage doubler rectifier circuit, and the like are provided within the housing 51.

An L-shaped radiation source attachment part 32 is provided at a tip (one end) of the arm part 40. The radiation generating part 50 is attached to the one end of the arm part 40 via the radiation source attachment part 32. As illustrated in FIGS. 1 and 2, the cable part 90 taken out from the one end of the arm part 40 is connected to the radiation generating part 50 via a connector.

The radiation generating part 50 is connected to the radiation source attachment part 32 so as to be rotationally movable with an axis AX2 as a rotational movement axis. The rotational movement axis AX2 is an axis that extends in the leftward-rightward direction (x direction). In addition, the radiation source attachment part 32 holds the radiation generating part 50 such that the radiation generating part 50 moves rotationally via a friction mechanism. For this reason, the radiation generating part 50 is rotationally movable by applying a certain degree of strong external force, does not move rotationally unless an external force is applied, and maintains a relative angle with respect to the arm part 40.

Figure 6:
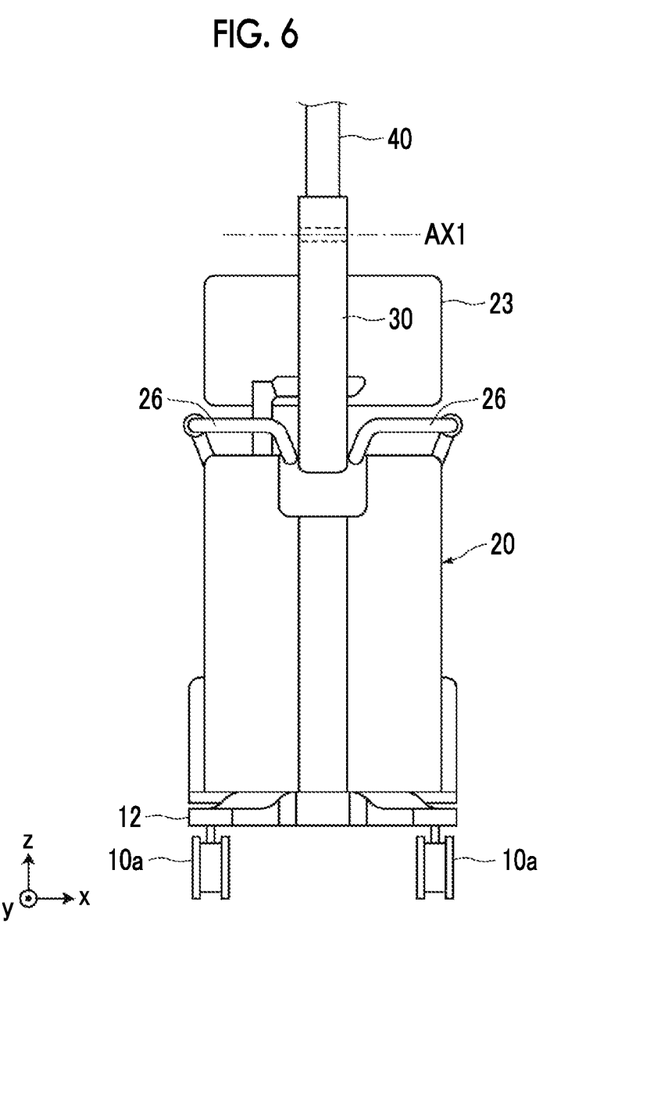
FIG. 6 is a view of the radiation irradiation device illustrated in FIG. 1 as seen from the front.

Additionally, the monitor 23 is attached to an upper surface of the housing 21. Additionally, a handle part 26 for pushing or pulling the radiation irradiation device 1 is attached to an upper part of the housing 21. The handle part 26 is provided so as to go around the housing 21, and is configured so as to be capable of being held not only from a rear side of the radiation irradiation device 1 but also from a front side or a lateral side. FIG. 6 is a view of the radiation irradiation device 1 as seen from the front. As illustrated in FIG. 6, the handle part 26 is provided so as to go around to a front side of the main body part 20.

The monitor 23 consists of a liquid crystal panel or the like, and displays a radiation image acquired by imaging of a subject, and various kinds of information required for the control of the radiation irradiation device 1. Additionally, the monitor 23 includes the touch panel type input part 24, and receives input of various instructions required for the operation of the radiation irradiation device 1. Specifically, input for setting of imaging conditions and input for imaging, that is, emission of radiation, can be received. The monitor 23 is attached to the upper surface of the housing 21 so as to be capable of changing the inclination and the rotational position of a display surface with respect to the horizontal direction. Additionally, instead of the touch panel type input part 24, buttons for performing various operations may be included as the input part.

One end of the supporting member 30 is connected to the other end of the arm part 40. The arm part 40 is connected to the supporting member 30 so as to be rotationally movable with an axis AX1 as a rotational movement axis. The rotational movement axis AX1 is an axis that extends in the leftward-rightward direction (x direction). The arm part 40 moves rotationally in a direction of arrow A illustrated in FIG. 2 such that an angle formed with the supporting member 30 is changed about the rotational movement axis AX1.

A rotational movement part 31 having the rotational movement axis AX1 holds the arm part 40 such that the arm part 40 moves rotationally via the friction mechanism. For this reason, the arm part 40 is rotationally movable by applying a certain degree of strong external force, does not move rotationally unless an external force is applied, and maintains a relative angle with respect to the supporting member 30.

In addition, although the rotational movement of the arm part 40 and the radiation generating part 50 is performed via the friction mechanism, rotational movement positions of these parts may be fixed by a well-known locking mechanism. In this case, the rotational movements of the arm part 40 and the radiation generating part 50 become possible by releasing the locking mechanism. The rotational movement positions can be fixed by locking the locking mechanism at desired rotational movement positions.

The other end of the supporting member 30 is connected to the surface of the main body part 20 on the front side. The supporting member 30 is provided so as to be fixed with respect to the main body part 20, and is attached so as to be non-rotatable with respect to the main body part 20. In the present embodiment, as described above, the orientation of the arm part 40 can be freely changed together with the main body part 20 by the revolution of the first casters 10a and the second casters 10b. Thus, it is not necessary to make the supporting member 30 have a degree of freedom, and a simpler configuration can be adopted. However, the invention is not limited to this, and the supporting member 30 may be configured to rotate with emphasis on handleability. That is, the supporting member 30 may be configured so as to be rotatable with an axis passing through the center of the portion of the supporting member 30 connected to the main body part 20 and extending in the vertical direction as a rotation axis.

In the present embodiment, when a subject is imaged, as illustrated in FIG. 2, the imaging is performed by arranging a radiation detector 86 under a subject H that lies on ones' back on a bed 3 and irradiating the subject H with the radiation emitted from the radiation generating part 50. In addition, the radiation detector 86 and the radiation irradiation device 1 are connected together with or without wires. Accordingly, the radiation image of the subject H acquired by the radiation detector 86 is directly input to the radiation irradiation device 1.

Figure 7:
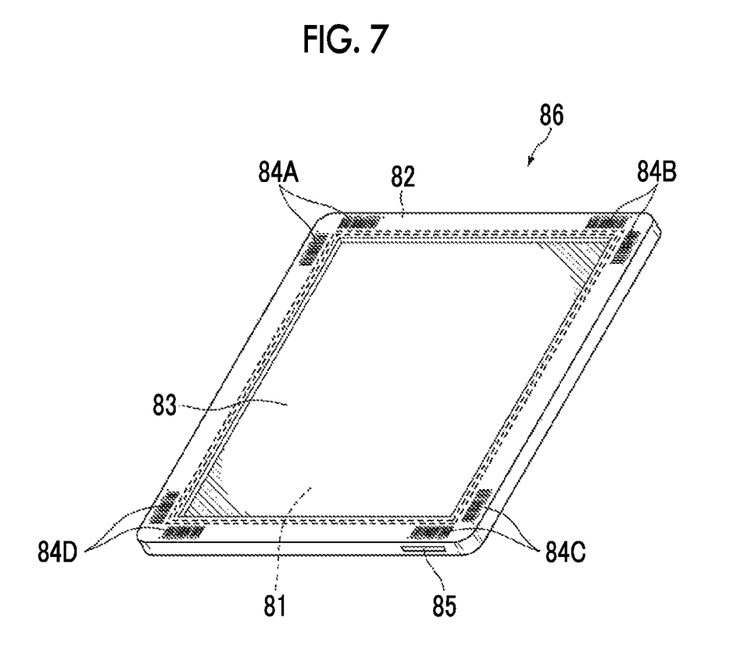
FIG. 7 is an external perspective view of a radiation detector as seen from a radiation detection surface side.

Here, a radiation detector 86 will be briefly described with reference to FIG. 7. FIG. 7 is an external perspective view of the radiation detector as seen from a front surface that is a radiation detection surface side. As illustrated in FIG. 7, the radiation detector 86 is a cassette type radiation detector including a housing 82 that has a rectangular flat plate shape and houses a detecting part 81. The detecting part 81 includes a scintillator (fluorescent body) that converts incident radiation into visible light as is well known, and a thin film transistor (TFT) active matrix substrate. A rectangular imaging region where a plurality of pixels that accumulate electrical charge according to the visible light from the scintillator are arrayed is forming on the TFT active matrix substrate.

Additionally, the housing 82 includes a round-chamfered metallic frame. A gate driver that gives a gate pulse to a gate of a TFT to switch the TFT, an imaging control part including, a signal processing circuit that converts an electrical charge accumulated in a pixel into an analog electrical signal representing an X-ray image to output the converted signal, and the like in addition to the detecting part 81 are built in the housing. Additionally, the housing 82 has, for example, a size based on International Organization for Standardization (ISO) 4090:2001 that is substantially the same as a film cassette, an imaging plate (IP) cassette, and a computed radiography (CR) cassette.

A transmission plate 83 that allows radiation to be transmitted therethrough is attached to a front surface of the housing 82. The transmission plate 83 has a size that substantially coincides with a detection region of radiation in the radiation detector 86, and is formed of a carbon material that is lightweight, has high rigidity, and has high radiation transmissivity. In addition, the shape of the detection region is the same oblong shape as the shape of the front surface of the housing 82. Additionally, the portion of the frame of the housing 82 protrudes from the transmission plate 83 in a thickness direction of the radiation detector 86. For this reason, the transmission plate 83 is not easily damaged.

Markers 84A to 84D showing identification information for identifying the radiation detector 86 are applied to four corners of the front surface of the housing 82. In the present embodiment, the markers 84A to 84D consist of two bar codes that are orthogonal to each other, respectively.

Additionally, a connector 85 for charging the radiation detector 86 is attached to a side surface of the housing 82 on the markers 84C, 84D side.

When the radiation irradiation device 1 according to the present embodiment is used, the operator rotationally moves the arm part 40 around the rotational movement axis AX1 in an illustrated counterclockwise direction from an initial position of the arm part 40 illustrated in FIG. 1, and thereby the radiation generating part 50 is moved to a target position immediately above the subject H, as illustrated in FIG. 2. The radiation image of the subject H can be acquired by driving the radiation generating part 50 according to an instruction from the input part 24 to irradiate the subject H with radiation and detecting the radiation transmitted through the subject H, using the radiation detector 86, after the radiation generating part 50 is moved to the target position.

In addition, as the radiation detector 86, as described above, it is desirable to use a radiation detector in which the scintillator and the TFT active matrix substrate including light receiving elements are laminated and which receives irradiation of radiation from a TFT active matrix substrate side (a side opposite to a scintillator side). By using such a high-sensitivity radiation detector 86, a low-output radiation source can be used as the radiation generating part 50, and the weight of the radiation generating part 50 can be made light. In addition, generally, the radiation source output of the radiation generating part 50 and the weight of the radiation generating part 50 are in a proportional relation.

Since the weight of the radiation generating part 50 can be made light as described above, the total weight of the radiation irradiation device 1 can also be made light.

Accordingly, by using the revolving casters as the second caster 10b (rear wheels) as in the radiation irradiation device 1 of the present embodiment, the revolution performance of the radiation irradiation device 1 can be improved, and handling can be markedly improved.

In addition, the radiation source output of the radiation generating part 50 is preferably 15 kW or less, and is more preferably 4 kW or less. Additionally, the total weight of radiation irradiation device 1 is preferably 120 kg or less, and is more preferably 90 kg or less.

Next, a configuration in which the radiation detector 86 in the main body part 20 is capable of being housed will be described. As illustrated in FIGS. 1 and 2, the housing 21 of the main body part 20 has a flat surface 21a inclined to a supporting member 30 side, on a surface opposite to a side where the supporting member 30 is attached, and the flat surface 21a is provided with the cradle 25.

An insertion port 25a for inserting the radiation detector 86 is formed in an upper surface of the cradle 25. The insertion port 25a has an elongated shape of a size such that the radiation detector 86 is fitted thereto. In the present embodiment, one end part on a side having the connector 85 of the radiation detector 86 is inserted to the insertion port 25a. Accordingly, this one end part is supported by a bottom part of the cradle 25, and the radiation detector 86 is held by the cradle 25. In this case, a front surface of the radiation detector 86 is directed to a flat surface 21a side.

A connector 25b is attached to the bottom part of the cradle 25. The connector 25b is electrically connected to the connector 85 of the radiation detector 86 when the radiation detector 86 is held by the cradle 25. The connector 25b is electrically connected to the battery part 60. Hence, when the radiation detector 86 is held by the cradle 25, the radiation detector 86 is charged by the battery part 60 via the connector 85 of the radiation detector 86 and the connector 25b of the cradle 25.

In addition, a configuration in which the radiation detector 86 is chargeable by the battery part 60 has been described in the present embodiment. As described above, a configuration in which the monitor 23 is chargeable by the battery part 60 may be adopted. Moreover, a configuration in which an external connector is further provided at the main body part 20 and external instruments other than the monitor are connectable may be adopted. Also, a configuration in which electric power is supplied to an external instrument by the battery part 60 via the external connector and the external instrument is chargeable may be adopted. As the external instrument, for example, there is a note-type computer used as a console, or the like.

In addition, the radiation irradiation device of the invention does not necessarily include the leg part 10 as in the radiation irradiation device 1 of the above embodiment. Additionally, the configuration of the supporting member 30 and the arm part 40 is not limited to the configuration of the above embodiment, and other configurations may be adopted.

EXPLANATION OF REFERENCES

1: radiation irradiation device
2: device placement surface
3: bed
10: leg part
10a: first caster
10b: second caster
11: pedestal part
12: foot arm part 12a: tip part
13: pedal part
13a: first pedal
13b: second pedal
20: main body part
21: housing
21a: flat surface
22: control part
22a: residual capacity calculation part
22b: notification part
23: monitor
24: input part
25: cradle
25a: insertion port
25b: connector
26: handle part
30: supporting member
31: rotational movement part
32: radiation source attachment part
40: arm part
50: radiation generating part
51: housing
60: battery part
70: current and voltage measuring part
80: radiation exposure switch
80a: exposure SW1
80b: exposure SW2
81: detecting part
82: housing
83: transmission plate
84A to 84D: marker
85: connector
86: radiation detector
90: cable part
AX1: rotational movement axis
AX2: rotational movement axis
H: subject

What is claimed is:

1. A radiation irradiation device comprising:
an x-ray radiation generator comprising an x-ray source for generating x-rays;
a battery that supplies electric power to the x-ray radiation generator;
a computer that calculates the residual capacity of the battery;
a first exposure switch that receives a preparation operation start instruction of the x-ray radiation generator; and
a second exposure switch that receives an emission instruction of the x-rays from the x-ray radiation generator,
wherein the computer calculates the residual capacity of the battery on the basis of a current drawn from the battery by the x-ray source, an internal resistance of the battery, and a voltage of the battery,
wherein the computer calculates the internal resistance of the battery on the basis of a current drawn from the battery by the x-ray source and a voltage of the battery at a first time point and a current drawn from the battery by the x-ray source and a voltage of the battery at a second time point different from the first time point,
wherein the first time point is a time point when the first exposure switch receives the preparation operation start instruction, and the second time point is a time point after the first time point and before the second exposure switch receives the emission instruction.

2. The radiation irradiation device according to claim 1, wherein the computer calculates the internal resistance R of the battery on the basis of the following Expression, $R=(V1-V2)/(I1-I2)$ where, I1 is the current drawn from the battery at the first e point, V1 is the voltage of the battery at the first time point, I2 is the current drawn from the battery at the second time point, and V2 is the voltage of the battery at the second time point.

3. The radiation irradiation device according to claim 2, wherein the computer calculates the residual capacity of the battery in a period other than a generation period of the x-rays.

4. The radiation irradiation device according to claim 3, further comprising:
wherein the computer calculates the residual capacity of the battery in a period other than a period in which the second exposure switch is turned on.

5. The radiation irradiation device according to claim 3, wherein the computer calculates the residual capacity of the battery in a period other than a period until the second exposure switch is turned off from lapse of a preset period after the first exposure switch is turned on.

6. The radiation irradiation device according to claim 2, further comprising:
a notification part that performs notification that the residual capacity of the battery calculated by the computer s equal to or less than a preset threshold value.

7. The radiation irradiation device according to claim 1, wherein the computer calculates the residual capacity of the battery in a period other than a generation period of the x-rays.

8. The radiation irradiation device according to claim 7, further comprising:
wherein the computer calculates the residual capacity of the battery in a period other than a period in which the second exposure switch is turned on.

9. The radiation irradiation device according to claim 7, wherein the computer calculates the residual capacity of the battery in a period other than a period until the second exposure switch is turned off from lapse of a preset period after the first exposure switch is turned on.

10. The radiation irradiation device according to claim 1, wherein the computer calculates the internal resistance of the battery at preset intervals.

11. The radiation irradiation device according to claim 1, further comprising:
a notification part that performs notification that the residual capacity of the battery calculated by the computer is equal to or less than a preset threshold value.

12. The radiation irradiation device according to claim 1, further comprising:
a notification part that performs notification that the residual capacity of the battery calculated by the computer is equal to or less than a preset threshold value.

13. The radiation irradiation device according to claim 1, further comprising:
a control part that stops the radiation irradiation device in a case where the residual capacity of the battery calculated by the computer is equal to or less than a preset threshold value.

14. A radiation irradiation device comprising:
an x-ray radiation generator comprising an x-ray source for generating x-rays;

a battery that supplies electric power to the x-ray radiation generator; and a computer that calculates the residual capacity of the battery, wherein the computer calculates the residual capacity of the battery on the basis of a current drawn from the battery by the x-ray source, an internal resistance of the battery, and a voltage of the battery, wherein the computer calculates the internal resistance of the battery on the basis of a current drawn from the battery by the x-ray source and a voltage of the battery at a first time point and a current drawn from the battery by the x-ray source and a voltage of the battery at a second time point different from the first time point, wherein the first time point is during the generation period of the x-rays and the second time point is a period other than the generation period of the x-rays.

15. A radiation irradiation device comprising:

an x-ray radiation generator comprising an x-ray source for generating x-rays;

a battery that supplies electric power to the x-ray radiation generator; and a computer that calculates the residual capacity of the battery, wherein the computer calculates the residual capacity of the battery on the basis of a current drawn from the battery by the x-ray source, an internal resistance of the battery, and a voltage of the battery, wherein the computer calculates the internal resistance of the battery on the basis of a current drawn from the battery by the x-ray source and a voltage of the battery at a first time point and a current drawn from the battery by the x-ray source and a voltage of the battery at a second time point different from the first time point, wherein the first time point is a period of a normal electric power supply mode and the second time point is a period of an electric power supply saving mode, wherein electric power is supplied from the battery to entire components of the radiation irradiation device during the normal electric power supply mode, and the electric power is kept from being supplied to at least one component of the radiation irradiation device during the electric power supply saving mode.

* * * * *